(12) United States Patent
Govrin-Yehudian et al.

(10) Patent No.: US 7,988,731 B2
(45) Date of Patent: Aug. 2, 2011

(54) LIGHTWEIGHT IMPLANTABLE PROSTHETIC DEVICE

(75) Inventors: Jacky Govrin-Yehudian, Caesarea (IL); Betty Orit Govrin-Yehudian, Caesarea (IL); Dael Govreen-Segal, Hod Hasharon (IL)

(73) Assignee: G & G Biotechnology Ltd, Haifa (IL)

( * ) Notice: Subject to any disclaimer, the term of this patent is extended or adjusted under 35 U.S.C. 154(b) by 459 days.

(21) Appl. No.: 11/919,069

(22) PCT Filed: Apr. 24, 2006

(86) PCT No.: PCT/IL2006/000501
§ 371 (c)(1),
(2), (4) Date: Oct. 23, 2007

(87) PCT Pub. No.: WO2006/114786
PCT Pub. Date: Nov. 2, 2006

(65) Prior Publication Data
US 2009/0299473 A1    Dec. 3, 2009

Related U.S. Application Data

(60) Provisional application No. 60/674,336, filed on Apr. 25, 2005, provisional application No. 60/698,973, filed on Jul. 14, 2005.

(51) Int. Cl.
*A61F 2/12* (2006.01)
(52) U.S. Cl. .................................... 623/8; 623/7
(58) Field of Classification Search .................. 623/7, 8, 623/23.72–23.74; 128/DIG. 21, 899
See application file for complete search history.

(56) References Cited

U.S. PATENT DOCUMENTS

| | | | |
|---|---|---|---|
| 3,681,787 A | 8/1972 | Perras | 3/36 |
| 3,683,424 A | 8/1972 | Pangman | 3/36 |
| 3,811,133 A * | 5/1974 | Harris | 623/7 |
| 3,986,213 A * | 10/1976 | Lynch | 623/8 |
| 4,019,209 A | 4/1977 | Spence | 3/36 |
| 4,298,998 A | 11/1981 | Naficy | 3/36 |
| 4,380,569 A | 4/1983 | Shaw | 428/283 |
| 4,470,160 A | 9/1984 | Cavon | 3/36 |
| 4,676,795 A | 6/1987 | Grundei | 623/8 |
| 4,681,587 A | 7/1987 | Eberl et al. | 623/7 |
| 4,773,909 A | 9/1988 | Chaglassian | 623/8 |
| 4,795,464 A | 1/1989 | Eberl et al. | 623/8 |

(Continued)

FOREIGN PATENT DOCUMENTS

WO    WO96/32908    10/1996
(Continued)

OTHER PUBLICATIONS

EP search report for EP 06728299.6, Apr. 27, 2010.
(Continued)

*Primary Examiner* — David Isabella
*Assistant Examiner* — Yashita Sharma
(74) *Attorney, Agent, or Firm* — Graeser Assoc. International; Dvorah Graeser

(57) ABSTRACT

A reduced weight implantable prosthesis, including, an outer surface shell for encapsulating the prosthesis, a gel mixture comprising a mixture of a cohesive gel and micro-spheres for filling the shell, one or more inner volumes internal to the shell which do not contain the gel mixture; and wherein the gel mixture contains less than 60% by volume of micro-spheres mixed into the cohesive gel.

27 Claims, 3 Drawing Sheets

U.S. PATENT DOCUMENTS

| | | | | |
|---|---|---|---|---|
| 5,147,398 | A | | 9/1992 | Lynn et al. ............................... 623/8 |
| 5,171,269 | A | * | 12/1992 | Bark ......................................... 623/8 |
| 5,236,454 | A | | 8/1993 | Miller ...................................... 623/8 |
| 5,246,454 | A | | 9/1993 | Peterson .................................. 623/8 |
| 5,358,521 | A | | 10/1994 | Shane ...................................... 623/8 |
| 5,407,445 | A | | 4/1995 | Tautvydas et al. ...................... 623/8 |
| 5,480,430 | A | | 1/1996 | Carlisle et al. .......................... 623/8 |
| 5,496,367 | A | * | 3/1996 | Fisher ...................................... 623/8 |
| 5,534,023 | A | | 7/1996 | Henley ..................................... 623/8 |
| 5,545,217 | A | | 8/1996 | Offray et al. ............................ 623/8 |
| 5,549,671 | A | * | 8/1996 | Waybright et al. ..................... 623/8 |
| 5,590,430 | A | | 1/1997 | Sereboff ................................ 5/655.5 |
| 5,653,755 | A | | 8/1997 | Ledergerber ............................ 623/8 |
| 5,658,330 | A | | 8/1997 | Carlisle et al. ........................ 623/11 |
| 5,723,006 | A | | 3/1998 | Ledergerber ............................ 623/8 |
| 5,741,877 | A | | 4/1998 | Tiffany .................................. 528/15 |
| 5,871,497 | A | | 2/1999 | Young ................................. 606/190 |
| 5,902,335 | A | | 5/1999 | Snyder, Jr. .............................. 623/7 |
| 6,146,418 | A | | 11/2000 | Berman ................................... 623/8 |
| 6,183,514 | B1 | | 2/2001 | Becker ..................................... 623/8 |
| 6,296,800 | B1 | | 10/2001 | Stelter et al. ........................ 264/267 |
| 6,464,726 | B1 | | 10/2002 | Heljenek ................................. 623/8 |
| 6,478,656 | B1 | | 11/2002 | Khouri ................................... 450/39 |
| 6,486,237 | B1 | | 11/2002 | Howe et al. ........................... 524/71 |
| 6,544,287 | B1 | | 4/2003 | Johnson et al. ......................... 623/7 |
| 6,835,763 | B2 | | 12/2004 | Ellis et al. ............................ 523/218 |
| 6,932,840 | B1 | | 8/2005 | Bretz ....................................... 623/8 |
| 6,967,221 | B2 | | 11/2005 | Meguriya .............................. 521/54 |
| 6,972,313 | B2 | | 12/2005 | Howe et al. ........................... 528/15 |
| 2002/0038147 | A1 | | 3/2002 | Miller, III .............................. 623/8 |
| 2002/0103539 | A1 | | 8/2002 | Stelter ..................................... 623/7 |
| 2002/0193878 | A1 | * | 12/2002 | Bowman et al. ........................ 623/7 |
| 2003/0074084 | A1 | | 4/2003 | Nakao ............................... 623/23.67 |
| 2004/0049269 | A1 | | 3/2004 | Corbitt, Jr. et al. ..................... 623/8 |
| 2004/0073305 | A1 | * | 4/2004 | Schneider-Nieskens ............... 623/7 |
| 2004/0153151 | A1 | | 8/2004 | Gonzales de Vicente .............. 623/8 |
| 2005/0197698 | A1 | | 9/2005 | Schneider-Nieskens ............... 623/7 |
| 2006/0025859 | A1 | | 2/2006 | Stelter et al. ............................ 623/7 |
| 2006/0136056 | A1 | | 6/2006 | Wohl ....................................... 623/8 |
| 2006/0161266 | A1 | | 7/2006 | Schwibner et al. ............... 623/23.67 |
| 2006/0224239 | A1 | | 10/2006 | Tiahrt ...................................... 623/8 |
| 2007/0050026 | A1 | | 3/2007 | Carvalio .................................. 623/8 |
| 2007/0050027 | A1 | | 3/2007 | McGhan et al. ........................ 623/8 |
| 2007/0135916 | A1 | | 6/2007 | Maxwell et al. ........................ 623/8 |
| 2007/0293945 | A1 | | 12/2007 | Snyder .................................... 623/7 |
| 2009/0299472 | A1 | | 12/2009 | Huang ..................................... 623/7 |

FOREIGN PATENT DOCUMENTS

| | | |
|---|---|---|
| WO | WO97/19654 | 6/1997 |
| WO | WO03/026866 | 4/2003 |
| WO | WO2005020843 | 3/2005 |
| WO | PCT/IL06/00501 | 4/2006 |

OTHER PUBLICATIONS

Search report for corresponding EP application 06728299.6, Issued Apr. 27, 2010.

* cited by examiner

LIGHTWEIGHT IMPLANTABLE PROSTHETIC DEVICE

CROSS-REFERENCE TO RELATED APPLICATIONS

This application is the U.S. national phase application of PCT International Application No. PCT/IL2006/000501, filed on 24 Apr. 2006, which claims the benefit of U.S. Provisional Application Ser. No. 60/674,336, filed on 25 Apr. 2005, and U.S. Provisional Application Ser. No. 60/698,973, filed on 14 Jul. 2005, all of which are hereby incorporated by reference in their entirety.

RELATED APPLICATIONS

The current application claims priority from U.S. provisional application No. 60/674,336 titled "implantable prosthetic device and method of usage of the same" filed Apr. 25, 2005, and U.S. provisional application No. 60/698,973 titled "implantable prosthetic device and method of usage of the same" filed Jul. 27, 2005, the disclosures of which are incorporated herein by reference.

FIELD OF THE INVENTION

The present invention relates generally to implantable prosthetic devices and specifically to implantable prosthetic devices of reduced weight.

BACKGROUND OF THE INVENTION

In the last century reconstructive and cosmetic surgery has become a common practice. Specifically cosmetic breast surgery has been developed to allow reconstruction of a woman's breast that was affected by procedures such as mastectomy. Cosmetic breast surgery has also become available to amend the appearance of a woman's breast, for example by adding an implant to increase the size of the breast, to correct asymmetries, change shape and fix deformities.

Generally the implant is required to be able to provide a specific form and maintain the form for many years, preferably for the lifetime of the woman in which the implant is installed to prevent the need for additional invasive surgery. The implant is also required to have a specific feel preferably imitating the feel of a real breast. The implant also needs to be bio-durable such that it is not ruined by interaction with the human body and it needs to be bio-compatible so that the woman's health is not detrimentally affected by the implant even under extreme circumstances, for example the implant is required to be non toxic in case of leakage from the implant.

The standard implants used today comprise an outer shell typically formed from vulcanized silicone or polyurethane, and an inner content typically formed from a silicone gel or saline. The specific weight of the commonly used filling materials is generally between 0.95 to 1.15 (grams per centimeter cube). An average implant may weigh between 50 to 1000 grams, or even more. The weight of the implant is an addition, which is not negligible for a person.

Over time breast implants are known to cause many problems, mostly related to the weight of the implant, for example: ptosis (i.e. sagging and deformity), breast tissue atrophy, prominence of the implant through breast tissue, back pain, and striae of the skin.

Traditionally, the silicone gels used had silicone oils with short polymers in them that leached out through the shell over time. Current implants involve the use of a shell with barrier layers to achieve very low permeability, and using a cohesive gel as the filling material. The cohesiveness ensures that the filling material does not leak out into the body, even in case of rupture of the shell.

An additional characteristic to be considered in selection of the filling material is the resilience, elasticity and pliability of the implant, which provides it with a specific feeling when being sensed. Generally it is desirable to provide an implant which provides a specific shape and mimics the feel of real human tissue at the position of the implant. It is important that the implant maintain its form and feel for extended periods, to prevent the need for additional surgery.

US patent application publication no. 2004/0153151 to Gonzales dated Aug. 5, 2004 of which the disclosure is incorporated herein by reference describes a breast prosthesis from silicone that is formed as a trabecular body or micro-cell body in order to obtain a prosthesis of lower density.

U.S. Pat. No. 4,380,569 to Shaw dated Apr. 19, 1983 of which the disclosure is incorporated herein by reference, describes a reduced weight breast prosthesis which is worn external to the human body or implanted into the human body. The breast prosthesis is comprised from a mixture of a silicone gel with glass micro-spheres.

U.S. Pat. No. 5,902,335 to Snyder, Jr. dated May 11, 1999 of which the disclosure is incorporated herein by reference, describes a reduced weight breast prosthesis which is worn external to the human body, based on the U.S. Pat. No. 4,380,569 to Shaw. Snyder states that the use of glass micro-spheres as described by Shaw results in a stiff product that does not mimic the human breast as well as silicone gel alone. Snyder describes a breast prosthesis having two sections. A first outer section filled with silicone gel that mimics the human breast and a second inner section of reduced weight to reduce the weight of the prosthesis.

U.S. Pat. No. 5,658,330, to Carlisle et al. dated Aug. 19, 1997 of which the disclosure is incorporated herein by reference, describes a molded silicone foam implant and method for making it.

SUMMARY OF THE INVENTION

An aspect of an embodiment of the invention relates to a reduced weight implantable prosthesis filled with a inner content that mimics the resilience and feel of real human tissue, for example, a reduced weight breast implant that mimics the resilience and feel of breast tissue. The specific gravity of the prosthesis of this invention can be reduced to as little as 0.3 g/cc or less. The weight reduction is achieved by creating one or more areas in the prosthesis that are void of silicone gel, and by using a reduced weight gel mixture to replace heavier silicone gels that are commonly used.

In an exemplary embodiment of the invention, the inner content is comprised of a filler material that is a gel mixture and comprises a cohesive silicone gel mixed with multiple particles such as micro-spheres. The multiple particles can be of varying sizes, textures, weight, shape, materials, permeability, specific gravity and may be in themselves comprised of multiple particles. In an exemplary embodiment of the invention, the inner content is encased in a low penetratable outer surface that is optionally, comprised from a biocompatible silicone or other material. The outer surface serves as an enclosure for holding the reduced weight inner content. In an exemplary embodiment of the invention, the micro-spheres used in the gel mixture have a diameter of less than 200 microns, for example between 30-40 microns. Optionally, up to 60% of the gel mixture by volume comprises micro-spheres. In some embodiments of the invention, microspheres of larger diameter are used for preparing a gel mixture. Optionally, a mixture with larger micro-spheres (e.g. with a diameter of up to 500 microns or even up to 1000 microns) has a lower specific gravity than a mixture with smaller micro-spheres with similar wall thickness. In some embodiments of the invention, the prosthesis' inner content may be divided to multiple areas and different areas may utilize different filler material including different gel mixtures with a different specific gravity and possibly a different feel.

In an exemplary embodiment of the invention, an inner volume of the prosthesis is replaced with a filler material that is lighter than the gel mixture which is used to fill the rest of the prosthesis. Optionally, the gel mixture serves as padding surrounding the replaced inner volume to mimic the resilience and feel of real breast tissue, although the inner volume may not be as resilient as the gel mixture. In an exemplary embodiment of the invention, the resulting prosthesis achieves a weight reduction of up to 35%-70% or more. In some embodiments of the invention, the weight reduction of the prosthesis is achieved by providing a prosthesis with an inner volume filled with a foamy or sponge like silicone body surrounded by the gel mixture comprised from a mixture of a silicone gel and hollow micro-spheres. Optionally, the inner volume is encased in a low penetratable enclosure that is optionally, comprised from a biocompatible silicone. Optionally, the enclosure can be smooth or textured, with a round or anatomical or other shape.

In some embodiments of the invention, the inner volume is completely surrounded by the gel mixture to provide the required resilience. Alternatively, the inner volume is connected to one side of the outer surface, for example the side which does not face the surface skin of the person in order for the gel mixture to be sensed by external sensing and to reduce contact of the inner volume with external sensors. Optionally, the gel surrounding the spongy like body screens it and provides the required feel.

In an exemplary embodiment of the invention, the sponge like silicone body has a specific gravity, which is approximately 30-40% of the specific gravity of silicone gel, for example 0.35 g/cc. Optionally, the gel mixture described in the current application has a specific gravity in the range of 45%-75% of the specific gravity of a silicone gel without micro-spheres mixed in. In an exemplary embodiment of the invention, the micro-spheres have a specific gravity which is approximately between 10-40% of the specific gravity of silicone gel, for example between 0.1 g/cc to 0.4 g/cc.

In an exemplary embodiment of the invention, the inner volume may be filled with a gel mixture with larger micro spheres that has a lower specific gravity value than the gel mixture used to pad the inner volume.

In an exemplary embodiment of the invention, the reduced weight prosthesis may be provided in various sizes, for example extending from 50 CC to 1500 CC or larger or smaller. Optionally, a reduced weight prosthesis may be implanted in other areas of the body other than the breast, for example to replace or augment testicles, pectorals, a chin, cheeks, a calf, buttocks or other parts of the human or an animal body, while exhibiting tactile properties similar to natural tissue.

In some embodiments of the invention, the methods described above may be used to form an external prosthesis, which is worn external to the body under or as part of a person's clothes.

In some embodiments of the invention, the methods described above may be used as part of an implantable device or apparatus such as a cardiac pacemaker.

There is thus provided in accordance to an exemplary embodiment of the invention, a reduced weight implantable prosthesis, including, an outer surface shell for encapsulating the prosthesis, a gel mixture comprising a mixture of a cohesive gel and micro-spheres for filling the shell, one or more inner volumes internal to the shell which do not contain the gel mixture; and wherein the gel mixture contains less than 60% by volume of micro-spheres mixed into the cohesive gel. In an exemplary embodiment of the invention, the total volume of the one or more inner volumes is less than half of the volume of the prosthesis. Optionally, the total volume of the one or more inner volumes is less than a third of the volume of the prosthesis. In an exemplary embodiment of the invention, the total volume of the one or more inner volumes is greater than a quarter of the volume of the prosthesis. Optionally, the content of the one or more inner volumes has a specific gravity that is less than the specific gravity of the mixture.

In an exemplary embodiment of the invention, the content of at least one of the one or more inner volumes is a foamy silicone substance. Optionally, the content of at least one of the one or more inner volume is a silicone formed with a trabecular or micro-cell structure. In an exemplary embodiment of the invention, at least one of the one or more inner volumes comprise a silicone shell supported by a mechanical structure formed from silicone rods. Optionally, at least one of the one or more inner volumes comprise a self supporting hollow silicone shell.

In an exemplary embodiment of the invention, the one or more inner volumes are surrounded by the gel mixture. Optionally, at least one of the one or more inner volumes is approximately centered in the outer surface shell. In an exemplary embodiment of the invention, at least one of the one or more inner volumes is positioned adjacent to one side of the outer surface shell. Optionally, at least one of the one or more inner volumes is filled with a gel mixture with micro-spheres that have a larger diameter than the micro-spheres in the gel mixture external to the inner shell. In an exemplary embodiment of the invention, at least one of the inner volumes is subdivided to an internal outer layer and an internal inner volume. Optionally, the subdivided inner volume comprises content of different specific gravity values in the different subdivisions of the inner volume.

In an exemplary embodiment of the invention, the micro-spheres are hollow. Optionally, the gel mixture comprises micro-spheres of more than one size. In an exemplary embodiment of the invention, the micro-spheres are non-spherical. Optionally, the outer surface shell is formed from a low penetratable material. In an exemplary embodiment of the invention, the gel mixture masks the feel of the content of the one or more inner volumes. Optionally, the content of at least one of the one or more inner volumes comprises a gel mixture with micro-spheres of more than one size.

In an exemplary embodiment of the invention, the outer surface shell has a smooth outer surface. Alternatively, the outer surface shell has a textured outer surface. In an exemplary embodiment of the invention, the outer surface shell is round in shape. Optionally, the outer surface shell is anatomical in shape.

BRIEF DESCRIPTION OF THE DRAWINGS

The present invention will be understood and appreciated more fully from the following detailed description taken in conjunction with the attached drawings. Identical structures, elements or parts, which appear in more than one figure, are generally labeled with a same or similar number in all the figures in which they appear, wherein.

DETAILED DESCRIPTION

Figure 1:
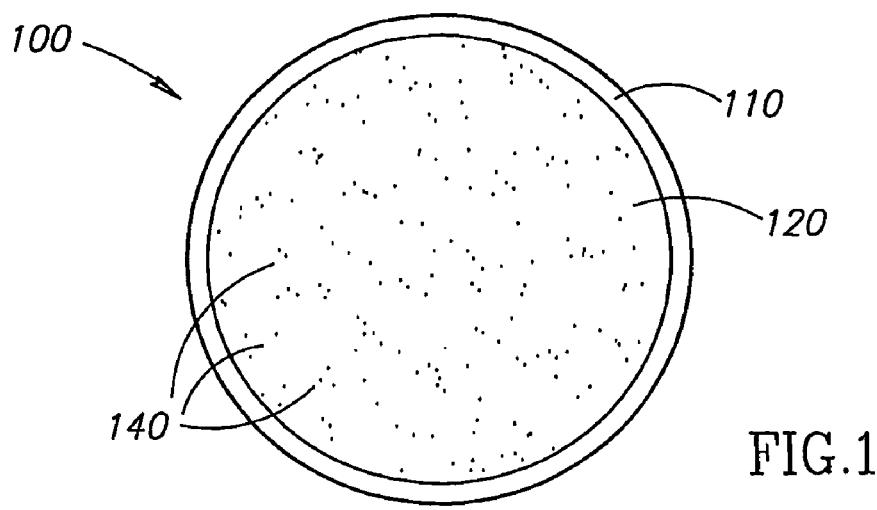
FIG. 1 is a schematic illustration of an implantable prosthesis filled with a gel mixture, according to an exemplary embodiment of the invention.

FIG. 1 is a schematic illustration of an implantable prosthesis 100 filled with a gel mixture 120, according to an exemplary embodiment of the invention. In an exemplary embodiment of the invention, prosthesis 100 comprises a low penetratable shell 110 that is optionally, comprised from a biocompatible silicone, polyurethane or other material as is commonly used for implants. Shell 110 may comprise a single layer or multiple layers, wherein some layers may be from one material and others from another. Additionally, shell 110 may be smooth or textured, with various patterns. Shell 110 can have areas of varying elasticity. Shell 110 can have a different thickness in different areas. Optionally, the material of shell 110 may be a combination of several materials. Generally, shell 110 serves as an enclosure for preventing the content of prosthesis 100 from leaking out. Optionally, shell 110 may be provided in various shapes, for example round, oval, anatomical, custom or other.

In an exemplary embodiment of the invention, gel mixture 120 is produced with a reduced specific gravity value to reduce the overall weight of the prosthesis. In an exemplary embodiment of the invention, gel mixture 120 is comprised from a medical grade cohesive silicone gel and reduced specific gravity particles, for example micro-spheres 140. Optionally, micro-spheres 140 may be provided with any shape and are not necessarily spherical. Optionally, the cohesive silicone gel is selected from materials which are not restricted for use inside the human body, although a low penetratable shell may be sufficient to allow other silicone gels since the shell prevents contact with the internal body of the person. An example of a gel not-restricted for internal use is Med3-6300, which is provided by Nusil technology, Carpintera, Calif. (www.nusil.com). Optionally, Med3-6300 is provided with a specific gravity value of 0.98 g/cc. It should be noted that a cohesive silicone gel generally maintains its form and requires a force to be applied to remove pieces from the gel once it is cured to a final form. In some embodiments of the invention, other types of gel materials may be used to form the mixture. The basic requirements of the material are to provide the correct feel, which mimics breast tissue, biocompatibility or at least being non-toxic. An example of such a material is Elast-Eon® which is manufactured by AorTech International plc, Surrey, United Kingdom.

In an exemplary embodiment of the invention, micro-spheres 140 are formed from plastic, ceramic, silicone, polymethyl methacrylate or glass although other materials may be used. Optionally, micro-spheres 140 provide a solid filling material which is hollow thus filling a relatively large volume while maintaining a relatively low weight. In an exemplary embodiment of the invention, micro-spheres with a diameter less than 200 microns or even less than 50 microns (e.g. 30-40 microns) are used to form gel mixture 120 in order to minimize any effect of micro-spheres 140 on the feel of gel mixture 120.

Micro-spheres are provided by many manufacturers, for example (a) Potters Industries Inc., Valley Forge, Pa., (b) 3M Company, St. Paul, Minn., (c) Sovereign Packaging Group Inc., Buffalo, N.Y. and others. Optionally, micro-spheres 140 provide a filling with a reduced specific gravity, for example "dualite" plastic micro-spheres manufactured by Sovereign with an average diameter of 30-40 microns have a specific gravity of 0.1 g/cc. other micro-spheres with similar diameter may be heavier (e.g. glass micro-spheres 0.34 g/cc at Potters) or lighter depending on the thickness of the surface of the spheres and the material used (e.g. glass microspheres K1 0.125 g/cc at 3M with an average diameter of 120 microns).

In some embodiments of the invention, the particle used (e.g. micro-spheres 140) may be electrically charged or neutral. They can be coated with a coating to improve adhesion, reduce permeability or augment other qualities.

In an exemplary embodiment of the invention, micro-spheres 140 are admixed into the silicone gel with a concentration of less than 60% or even less than 45% by volume. With 3M K1 spheres and the gel in the example above this requires less than 9-16% by weight, since one CC weighs approximately an eighth of the weight of the silicone gel. Likewise glass micro-spheres from potters require less than 26-35% by weight. Optionally, a higher concentration by volume would detrimentally affect the resilience and feel of the resulting mixture to an extent that it would be less appropriate for use in prosthesis 100.

In an exemplary embodiment of the invention, micro-spheres 140 are admixed into the silicone gel at room temperature. Optionally, the mixture is agitated to maintain a uniform distribution of micro-spheres 140. In an exemplary embodiment of the invention, a catalyst, for example a platinum catalyst is admixed with the micro-spheres to speed up the curing process, when heat is applied so that the micro-spheres will not manage to migrate to the surface during the curing thus providing a substantially uniform gel. Optionally, vacuum deaeration is recommended during the mixing process to removed trapped air bubbles. Alternatively, pressure may be applied to provide a uniform mixture. In an exemplary embodiment of the invention, the mixture is heated in an oven with a temperature of between 120° C. to 150° C. for approximately between 5-30 minutes. Optionally, the mixture is then post cured for a few hours (e.g. 4) with a temperature of 200° C. to remove volatile components and other residuals and to provide a full, stable cure. Optionally, other processes may be used to prepare gel mixture 120, for example using other temperatures ranges and time lengths.

In an exemplary embodiment of the invention, a mixture of 60% by volume of Med3-6300 silicone gel with 40% by volume 3M K1 micro-spheres provides a gel mixture 120 with the required resiliency and feel and a specific gravity of 0.71 g/cc. Optionally, a similar mixture with glass micro-spheres (manufactured by Potters) provides a gel mixture 120 with a specific gravity of approximately 0.79 g/cc. In some embodiments of the invention, glass micro-spheres are preferred over plastic due to their relatively inert characteristics, bio-compatibility and durability. In contrast plastic or other material micro-spheres may be preferred since they are lighter.

Optionally, gel mixture 120 would typically have a resilience characterized by a penetration measurement of approximately, between 4 to 150 mm/10 using a penetrometer with a 12 g 1" diameter shaft over 15 seconds.

In an exemplary embodiment of the invention, a desired amount (e.g. 400 cc) of gel mixture 120 is enclosed in shell 110 to form a reduced weight implantable prosthesis. Optionally, as described above a reduction in weight of 25-55 percent is achieved by the use of gel mixture 120 instead of the original silicone gel (e.g. Med3-6300). Optionally, shell 110 may be provided in various shapes, for example spherical, oval, teardrop/pear (sometimes referred to as anatomical) or custom shape.

In an exemplary embodiment of the invention the outer surface of shell 110 is provided with a smooth surface, a rough surface or a coated surface or with various textures to induce contact with the internal tissue of the person to secure the position of the implant and to prevent capsular contracture.

In an exemplary embodiment of the invention, the reduced weight prosthesis may be provided in various sizes, for example extending from 50 CC to 1500 CC or larger or smaller. Optionally, a reduced weight prosthesis may be implanted in other areas of the body other than the breast, for example to replace testicles, pectorals, a chin, cheeks, a calf, buttocks or other parts of the human or an animal body, while exhibiting properties similar to natural tissue. In some embodiments of the invention, the reduced weight prosthesis may be constructed for external use, for example to be worn under or as part of a person's clothes. Optionally, a reduced weight prosthesis will be used to replace an existing implant.

In some embodiments of the invention, a weight reduction greater than that achieved by the use of gel mixture 120 is desired. Optionally, gel mixture 120 can be used to circumvent a volume in the prosthesis with a content of even further reduced weight to reduce the overall weight of the prosthesis. Optionally, gel mixture 120 will interface shell 110 and provide the correct feel for the prosthesis, so that the inner volume can be provided by materials that do not necessarily have the desired resilient feel.

Figure 2A:
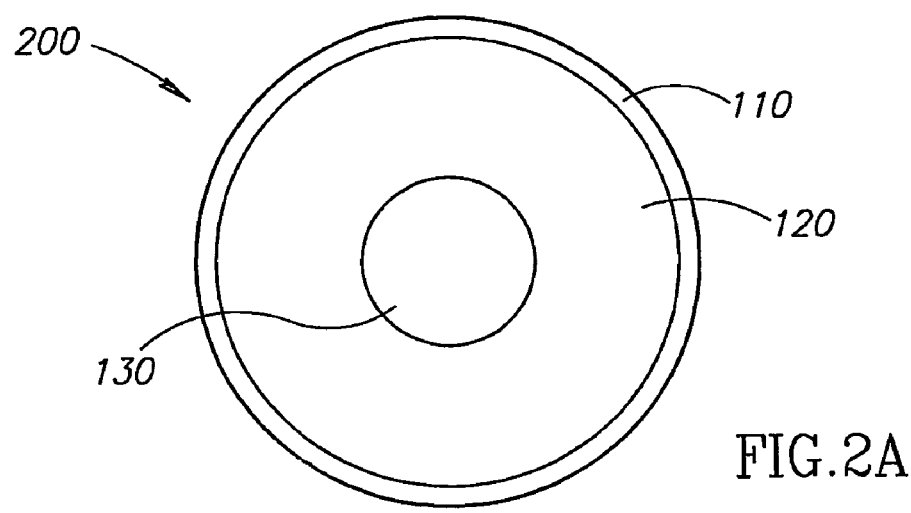
FIG. 2A is a schematic illustration of a prosthesis with a centered inner volume with a first filler material and an outer volume encasing the inner volume with a second filler material, according to an exemplary embodiment of the invention.
Figure 2B:
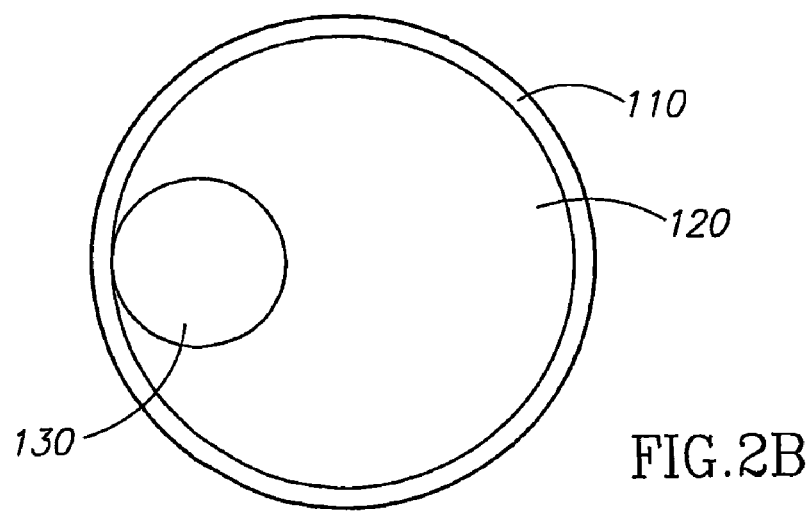
FIG. 2B is a schematic illustration of a prosthesis with a non-centered inner volume with a first filler material and an outer volume encasing the inner volume with a second filler material, according to an exemplary embodiment of the invention.

FIG. 2A is a schematic illustration of a prosthesis 200 with a centered inner volume 130 with a first filler material and an outer volume encasing the inner volume with a second filler material (e.g. gel mixture 120), according to an exemplary embodiment of the invention. Optionally, inner volume 130 may be positioned closer to one side of prosthesis 200, for example attached to shell 110 so that it may be positioned in the posterior, adjacent to the rib cage of the patient providing gel mixture 120 in the outer volume to face the anterior surface and provide the required resilient feel. FIG. 2B is a schematic illustration of prosthesis 200 with inner volume 130 with a first filler material in a non-centered position, and the outer volume encasing the inner volume with the second filler material (e.g. gel mixture 120), according to an exemplary embodiment of the invention.

Figure 3A:
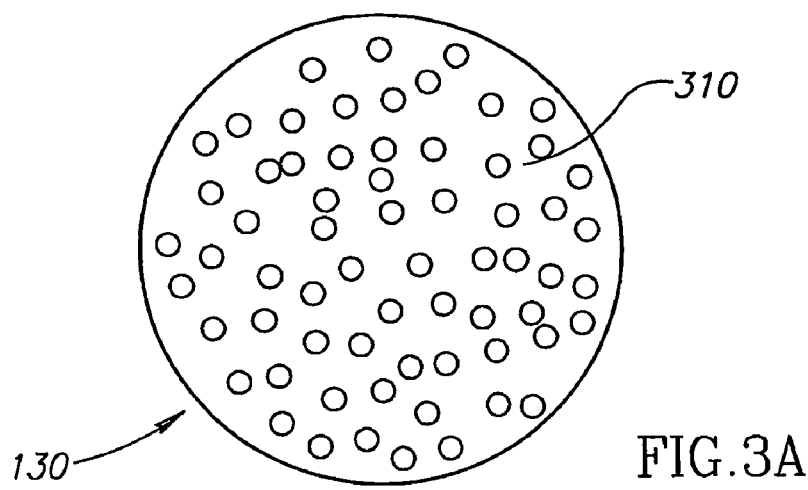
FIG. 3A is a schematic illustration of an inner volume with a foamy like structure, according to an exemplary embodiment of the invention.

FIG. 3A is a schematic illustration of inner volume 130 filled with a foamy like substance 310, according to an exemplary embodiment of the invention. In some embodiments of the invention, foamy like substance 310 may be provided by the use of a silicone foam, for example R-2350 provided by Nusil technology or Silastic® sponge system silicone rubber compound provided by Dow Corning Corp. (www.dowcorning.com). Dow Corning Corp publicizes that it offers spongy silicone prepared by mixing chemical blowing agents into the silicone before curing and also spongy silicone created in a process that uses water as the chemical agent for forming bubbles in the silicone. In an exemplary embodiment of the invention, foamy like substance 310 serves as a reduced weight filler for inner volume 130 due to the gas holes that are spaced throughout the substance. Typically foamy like substance 310 such as in the examples mentioned above, have a specific gravity that is approximately a third of the specific gravity of silicone gel. R-2350 has a specific gravity of 0.35 and Silastic® sponge system silicone rubber compound has a specific gravity of 0.37. In an exemplary embodiment of the invention, by providing an inner volume 130 as a third of the volume of prosthesis 200 the weight of prosthesis 200 may be reduced by approximately an additional 10% in addition to the reduction by using gel mixture 120. Optionally, the total reduction in weight achieved by the embodiment illustrated by FIG. 2B and FIG. 3A with inner volume 130 being a third of prosthesis 200 is between 35% to 65%. However a greater weight reduction may be achieved depending on the details described above, for example the type of micro-spheres used and the size of inner volume 130. In some embodiments of the invention, the size of inner volume 130 may be a quarter of the volume of prosthesis 200 or less. Alternatively the size of inner volume 130 may be a half of the volume of prosthesis 200 or larger.

In some embodiments of the invention, inner volume 130 is enclosed in a shell, for example similar to shell 110. Alternatively, inner volume 130 may be in direct contact with gel mixture 120 and not enclosed in a protective shell, depending on the filling materials used (e.g. a closed cell foam—does not absorb gel into the cells). Optionally, if gel mixture 120 is able to be absorbed by the filling material of inner volume 130 and cause shrinkage of the overall size of prosthesis 200, inner volume 130 would be enclosed in a protective shell.

In an exemplary embodiment of the invention, a gel mixture with micro-spheres of a larger diameter (e.g. 500 microns or 1000 microns) can be used to fill inner volume 130. Optionally, such a gel mixture has a lower specific gravity value, since the micro-spheres consume more space and have a larger hollow volume. In an exemplary embodiment of the invention, such a gel mixture may have a specific gravity value as low as 0.42 g/cc or less.

Figure 3B:
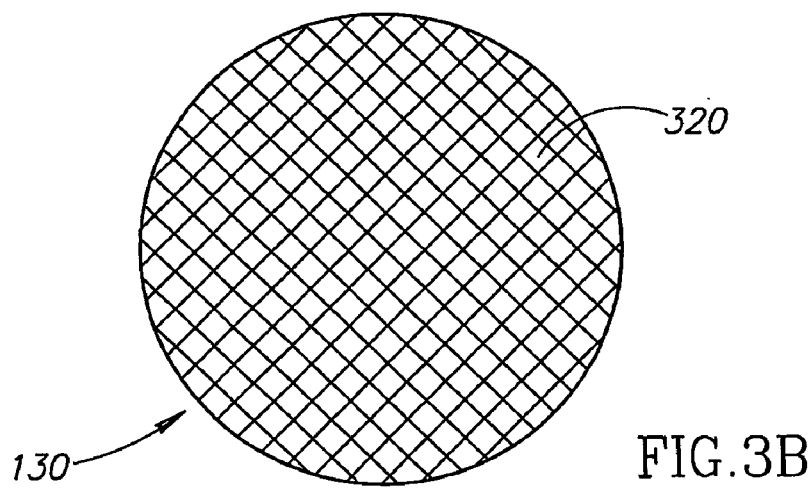
FIG. 3B is a schematic illustration of an inner volume with a compartment like structure, according to an exemplary embodiment of the invention.
Figure 3C:
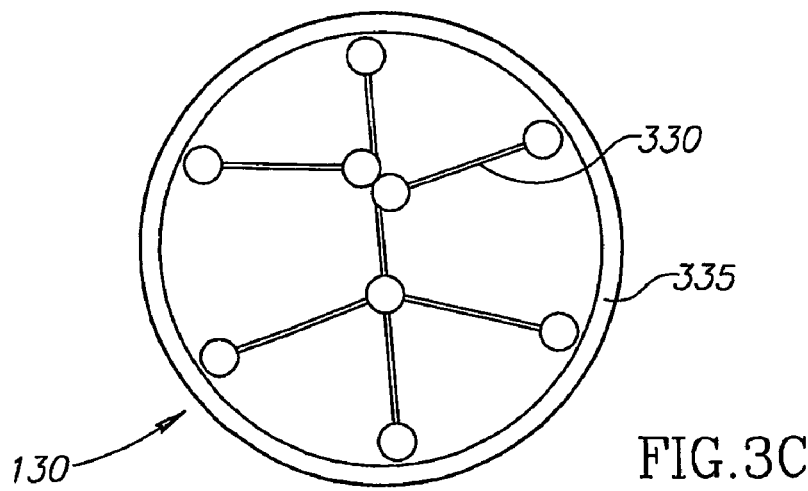
FIG. 3C is a schematic illustration of an inner volume with a three dimensional mechanical rod like structure, according to an exemplary embodiment of the invention.

FIG. 3B is a schematic illustration of inner volume 130 with a compartment like structure 320, according to an exemplary embodiment of the invention. Optionally, the filling material for inner volume 130 may be a silicone material with an orderly structure such as a hollow trabecular structure or hollow micro-cells. Optionally, such a structure has a specific gravity of 0.3-0.7 depending on specific geometry. In an exemplary embodiment of the invention, a compartment like structure 320 is formed by pouring uncured silicone rubber over a mold consisting of spherical or cuboidal projections, for example 2 mm high with a volume of 8 cubic millimeters and spaced 0.5 mm apart. The uncured silicone is poured to a depth of 2.5 mm and cured. The result is a sheet of 2.5 mm silicone with cavities open on one side. These sheets are adhesively attached together to provide a hollow cellular structure. Optionally, other methods may be used as known in the art FIG. 3C is a schematic illustration of inner volume 130 with a three dimensional mechanical rod like structure 330, according to an exemplary embodiment of the invention. Optionally, structure 330 forms a hollow volume with an encasing shell and rods to keep the shell from collapsing. In an exemplary embodiment of the invention, structure 330 is formed from a silicone substance using a single mold or multiple molds and then connected to form a three dimensional structure, as illustrated in FIG. 3C. In some embodiments of the invention, structure 330 is enclosed in an enveloping shell 335 to prevent gel mixture 120 from permeating into the hollow volume. In an exemplary embodiment of the invention, an inner volume 130, which fills a fifth of the volume of prosthesis 200 using structure 330 provides a total weight reduction of at least 15% since it is basically a hollow volume.

Figure 3D:
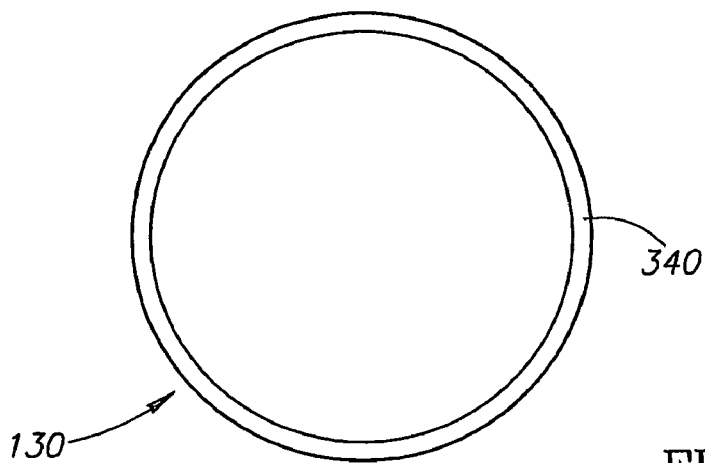
FIG. 3D is a schematic illustration of an inner volume with a self supporting surface structure, according to an exemplary embodiment of the invention.

FIG. 3D is a schematic illustration of inner volume 130 with a self supporting surface structure 340, according to an exemplary embodiment of the invention. Structure 340 forms a shell enclosing a hollow volume similar to structure 330, however structure 340 in contrast to structure 330 is self supporting and does not require rods to maintain its form.

In some embodiments of the invention, the embodiments described above for filling inner volume 130 provide an elastic volume filler, which in conjunction with gel mixture 120 provides prosthesis 200 with the required resilience and feel. Alternatively, the above suggested embodiments for inner volume 130 provide a relatively less elastic filler, and gel mixture 120 provides the padding to provide prosthesis 200 with the required resilience and feel in spite of inner volume 130.

Figure 4A:
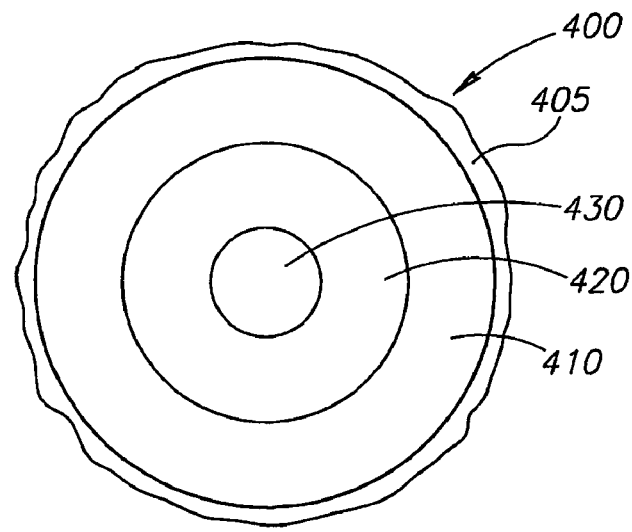
FIG. 4A is a schematic illustration of a concentric multi-layered prosthesis, according to an exemplary embodiment of the invention.

FIG. 4A is a schematic illustration of a concentric multi-layered prosthesis 400, according to an exemplary embodiment of the invention. In an exemplary embodiment of the invention, prosthesis 400 may comprise a shell 405 and multiple layers and compartments with optionally different types of fillings, for example the innermost layer 430 may comprise a hollow self supporting shell, the next layer 420 may comprise a foamy filling and the outer layer 410 may be filled with gel mixture 120. Alternatively, the layers may be arranged in any other order optionally, depending on the properties required for the resulting prosthesis. The compartments may be adjacent to each other or concentric or acentric. The compartments can be of different shapes and sizes. There may be barriers between the compartments or the filler materials in each compartment may interface gel mixture 120 and/or each other directly. The filler material in each compartment may be different or the same and a compartment may have more than one filler material. The boundary between compartments may be an abrupt or a gradual change in filler material properties, density or other characteristics.

In an exemplary embodiment of the invention, prosthesis 400 may comprise multiple layers and compartments in different shapes. Optionally, an anatomical shaped layer 430 may be located in proximity to the rib cage and constructed from a silicone foam, which is separated by a silicone barrier from layer 420. Optionally, layer 420 may comprise a gel mixture with a high concentration of large and small microspheres, for example 40% by volume of 120 micron microspheres mixed with 15% by volume of 30 micron microspheres and 45% by volume of silicone gel. Optionally, anterior layer 410 may be filled with a gel mixture of a low concentration such as 10% by volume of lightweight small particles with 90% by volume silicone gel. Optionally, there may or may not be a barrier (e.g. a shell) between high concentration layer 420 and low concentration layer 410. It should be noted that although FIG. 4 illustrates three layers or compartments—there may be more than three.

Figure 4B:
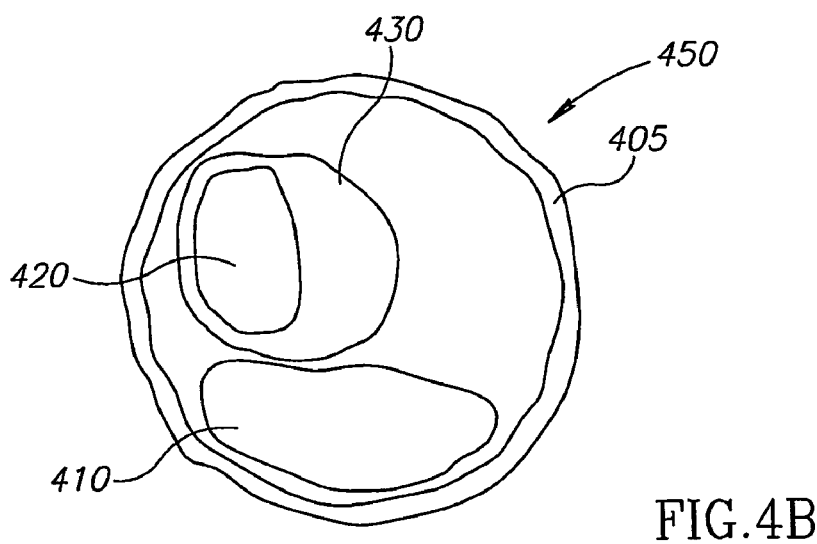
FIG. 4B is a schematic illustration of a prosthesis with multiple inner volumes, according to an exemplary embodiment of the invention

FIG. 4B is a schematic illustration of a prosthesis 450 with multiple inner volumes, according to an exemplary embodiment of the invention. In some embodiments of the invention, prosthesis 450 may comprise a shell 405 and multiple inner volumes (or layers) 410, 420, 430 similar to prosthesis 400. In FIG. 4B the inner volumes are shown placed next to each other (e.g. 410, 430) or internal to each other (e.g. 420, 430).

In some embodiments of the invention, different layers may be filled with gel mixtures with different sized microspheres. Optionally, the most outer layer comprises gel mixture 120, which provides a feel most conforming to real breast tissue. Other layers may be harder or less resilient but may reduce the overall weight of prosthesis 400.

In some embodiments of the invention, gel mixture 120 or other gel mixtures used for filling the prosthesis may comprise micro-spheres of multiple diameters. Optionally, the use of micro-spheres of multiple diameters allows better exploitation of the available volume, thus further reducing the specific gravity of gel mixture 120.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

Section headings are provided for assistance in navigation and should not be considered as necessarily limiting the contents of the section.

It will be appreciated by persons skilled in the art that the present invention is not limited to what has been particularly shown and described hereinabove. Rather the scope of the present invention is defined only by the claims, which follow.

The invention clamed is:

1. A reduced weight implantable breast prosthesis, comprising: a unitary outer surface shell for encapsulating the breast prosthesis; a gel mixture comprising a first gel mixture of a cohesive gel and particles for filling the shell; one or more inner volumes internal to the shell which do not contain said first gel mixture; wherein the first gel mixture contains less than 60% by volume of particles mixed into said cohesive gel, wherein said particles are microspheres, wherein at least one inner volume contains a second gel mixture having a greater percentage of microspheres by volume than said first gel mixture, wherein the second gel mixture of said one or more inner volumes has a specific gravity that is less than the specific gravity of said first gel mixture; wherein said one or more inner volumes containing the second gel mixture are less resilient than said first gel mixture; and wherein the implantable prosthesis is adapted for implantation in the breast.

2. A prosthesis according to claim 1, wherein the total volume of said one or more inner volumes is less than half of the volume of the prosthesis.

3. A prosthesis according to claim 1, wherein the total volume of said one or more inner volumes is less than a third of the volume of the prosthesis.

4. A prosthesis according to claim 1, wherein the total volume of said one or more inner volumes is greater than a quarter of the volume of the prosthesis.

5. A prosthesis according to claim 1, wherein said one or more inner volumes are surrounded by said first gel mixture.

6. A prosthesis according to claim 1, wherein at least one of said one or more inner volumes is approximately centered in said outer surface shell.

7. A prosthesis according to claim 1 wherein at least one of said one or more inner volumes is positioned adjacent to one side of said outer surface shell.

8. A prosthesis according to claim 1, wherein said second gel mixture microspheres have a larger diameter than the microspheres in the first gel mixture.

9. A prosthesis according to claim 1 wherein at least one of said inner volumes is subdivided to an internal outer layer and an internal inner volume.

10. A prosthesis according to claim 1, wherein said microspheres are hollow.

11. A prosthesis according to claim 1 wherein said first gel mixture comprises microspheres of more than one size.

12. A prosthesis according to claim 1, wherein said outer surface shell is formed from a low penetratable material.

13. A prosthesis according to claim 1, wherein said first gel mixture masks the feel of the content of said one or more inner volumes.

14. A prosthesis according to claim 1 wherein said second gel mixture comprises microspheres of more than one size.

15. A prosthesis according to claim 1 wherein said outer surface shell has a smooth outer surface.

16. A prosthesis according to claim 1, wherein said outer surface shell has a textured outer surface.

17. A prosthesis according to claim 1, wherein said outer surface shell is round in shape.

18. A prosthesis according to claim 1 wherein said outer surface shell is anatomical in shape.

19. The prosthesis of claim 1, wherein said microspheres are less than about 1000 microns in diameter.

20. The prosthesis of claim 19, wherein said microspheres are less than about 500 microns in diameter.

21. The prosthesis of claim 20, wherein said microspheres are less than about 200 microns in diameter.

22. The prosthesis of claim 1, wherein said microspheres comprise a material selected from the group consisting of plastic, ceramic, silicone, polymethyl methacrylate and glass.

23. The prosthesis of claim 1, wherein the specific gravity of said first gel mixture is up to about 0.8 g/cc.

24. The prosthesis of claim 23, wherein the specific gravity of said first gel mixture is up to about 0.4 g/cc.

25. The prosthesis of claim 24, wherein the specific gravity of said first gel mixture is up to about 0.3 g/cc.

26. The prosthesis of claim 1, wherein a total volume of the prosthesis is from about 50 cc to about 1500 cc.

27. A reduced weight implantable prosthesis, comprising: a unitary outer surface shell for encapsulating the prosthesis; a gel mixture comprising a first gel mixture of a cohesive gel and particles for filling the shell; one or more inner volumes internal to the shell which do not contain said first gel mixture; wherein the first gel mixture contains less than 60% by volume of particles mixed into said cohesive gel, wherein said particles are microspheres, wherein at least one inner volume contains a second gel mixture having a greater percentage of microspheres by volume than said first gel mixture, wherein the second gel mixture of said one or more inner volumes has a specific gravity that is less than the specific gravity of said first gel mixture; wherein said one or more inner volumes containing the second gel mixture are less resilient than said first gel mixture; and wherein the prosthesis is adapted for implantation in a location of a body of a subject selected from the group consisting of scrotum, pectoral, chin, cheek, calf and buttock.

* * * * *